(12) United States Patent
Proctor

(10) Patent No.: US 11,850,180 B2
(45) Date of Patent: Dec. 26, 2023

(54) URINE COLLECTION DEVICE

(71) Applicant: Gene Proctor, Las Vegas, NV (US)

(72) Inventor: Gene Proctor, Las Vegas, NV (US)

( * ) Notice: Subject to any disclaimer, the term of this patent is extended or adjusted under 35 U.S.C. 154(b) by 1065 days.

(21) Appl. No.: 16/696,560

(22) Filed: Nov. 26, 2019

(65) Prior Publication Data

US 2021/0154043 A1    May 27, 2021

(51) Int. Cl.
    *A61F 5/00*      (2006.01)
    *A61F 5/453*     (2006.01)
    *A61F 5/44*      (2006.01)

(52) U.S. Cl.
    CPC ............ *A61F 5/453* (2013.01); *A61F 5/4405* (2013.01)

(58) Field of Classification Search
    CPC .......... A61F 5/453; A61F 5/4405; A61F 5/44
    USPC ........................................................ 604/327
    See application file for complete search history.

(56) References Cited

U.S. PATENT DOCUMENTS

| | | | |
|---|---|---|---|
| 5,010,599 A | 4/1991 | Nilsson | |
| 5,331,689 A | 7/1994 | Haq | |
| 5,687,430 A * | 11/1997 | Itai | A61G 9/006 4/144.1 |
| 5,852,830 A * | 12/1998 | Horn | A47K 11/12 383/41 |
| 5,946,742 A * | 9/1999 | Parker | B60R 15/04 4/458 |
| 6,070,275 A * | 6/2000 | Garlock | A47K 11/12 4/144.1 |
| 6,684,414 B1 | 2/2004 | Rehrig | |
| 6,936,037 B2 * | 8/2005 | Bubb | A61M 1/74 604/327 |
| 8,046,848 B2 * | 11/2011 | Birbara | A61G 9/006 4/144.1 |
| 11,259,954 B2 * | 3/2022 | Gabriel | A61F 5/4405 |
| 2002/0193762 A1 | 12/2002 | Suydam | |

* cited by examiner

*Primary Examiner* — Andrew J Mensh

(57) ABSTRACT

A urine collection device for enabling urination while driving includes a tube that is flexible, a bag, and a pipe. The bag is selectively couplable to a first endpoint of the tube. The pipe is selectively couplable by a first end to a second endpoint of the tube so that the pipe is in fluidic communication with the bag. A second end of the pipe is configured to insert a penis of a user to position the pipe around the penis, thus enabling the user to urinate into the pipe. The tube is configured to allow flow of urine from the pipe to the bag.

17 Claims, 8 Drawing Sheets

URINE COLLECTION DEVICE

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION

(1) Field of the Invention

The disclosure relates to collection devices and more particularly pertains to a new collection device for enabling urination while driving.

(2) Description of Related Art Including Information Disclosed Under 37 CFR 1.97 and 1.98

The prior art relates to collection devices for urine, which may comprise a receptacle, a conduit, and an interface for a genitourinary area of a user.

BRIEF SUMMARY OF THE INVENTION

An embodiment of the disclosure meets the needs presented above by generally comprising a tube that is flexible, a bag, and a pipe. The bag is selectively couplable to a first endpoint of the tube. The pipe is selectively couplable by a first end to a second endpoint of the tube so that the pipe is in fluidic communication with the bag. A second end of the pipe is configured to insert a penis of a user to position the pipe around the penis, thus enabling the user to urinate into the pipe. The tube is configured to allow flow of urine from the pipe to the bag.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein.

DETAILED DESCRIPTION OF THE INVENTION

Figure 1:
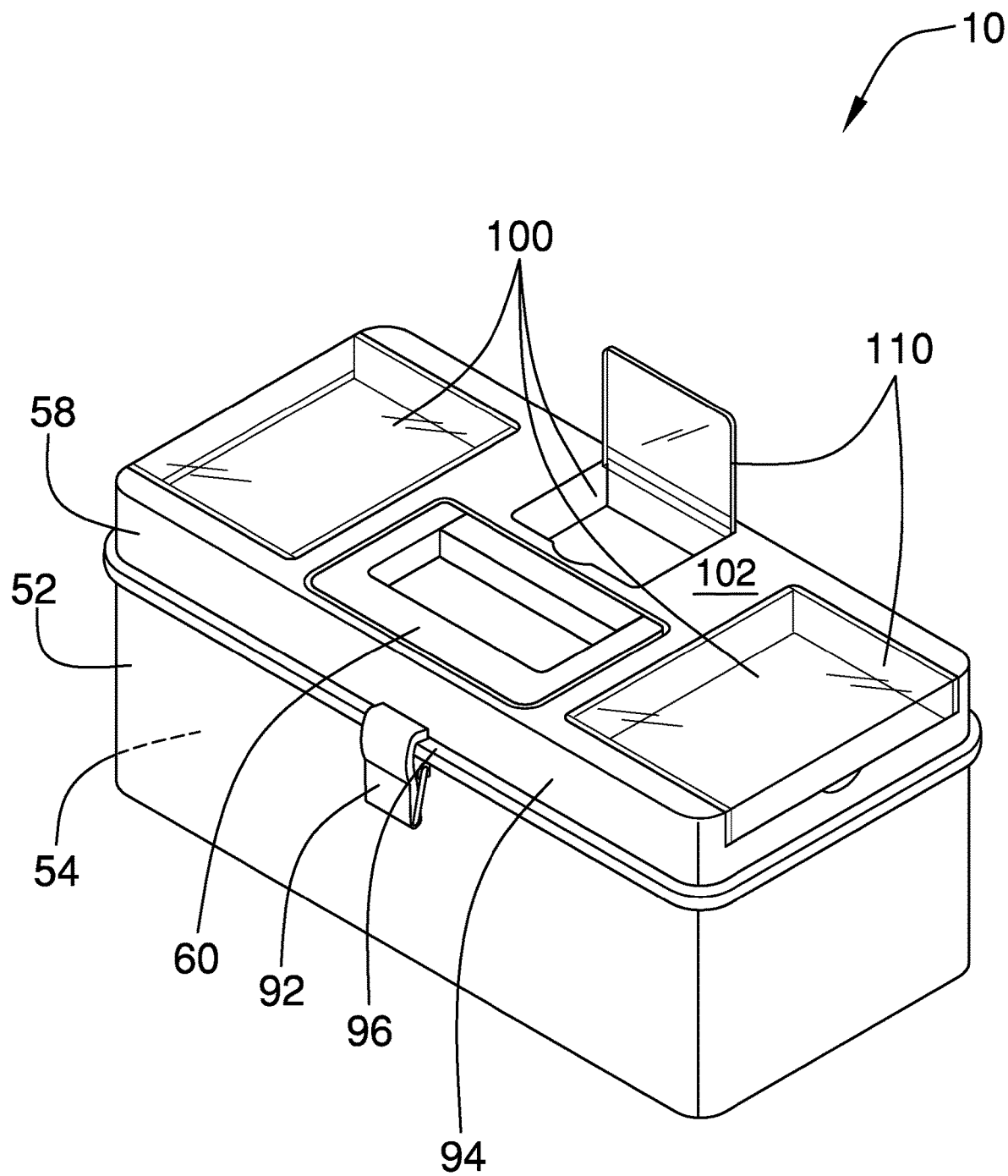
FIG. 1 is an isometric perspective view of a urine collection device according to an embodiment of the disclosure.

With reference now to the drawings, and in particular to FIGS. 1 through 8 thereof, a new collection device embodying the principles and concepts of an embodiment of the disclosure and generally designated by the reference numeral 10 will be described.

As best illustrated in FIGS. 1 through 8, the urine collection device 10 generally comprises a tube 12 that is flexible, a bag 14, and a pipe 16. The bag 14 is selectively couplable to a first endpoint 18 of the tube 12. The pipe 16 is selectively couplable by a first end 20 to a second endpoint 22 of the tube 12 so that the pipe 16 is in fluidic communication with the bag 14. A second end 24 of the pipe 16 is configured to insert a penis of a user to position the pipe 16 around the penis, thus enabling the user to urinate into the pipe 16. The tube 12 is configured to allow flow of urine from the pipe 16 to the bag 14. The device 10 might be used by a driver, such as a long-haul trucker, so that the driver can avoid stopping to urinate.

The pipe 16 may be conically shaped adjacent to the first end 20 so that the urine is directed to the tube 12. The pipe 16 may be substantially transparent so that urine in the pipe 16 is visible to the user. The pipe 16 may comprise plastic, or other substantially rigid material, such as, but not limited to, glass, metal, and the like.

A first conduit 26 and a second conduit 28 are coupled to the bag 14 and the pipe 16, respectively. The first conduit 26 is circumferentially larger than the tube 12 so that the first conduit 26 is positioned to selectively insert the first endpoint 18 of the tube 12 to removably couple the tube 12 to the bag 14. The second conduit 28 is circumferentially smaller than the tube 12 so that the second endpoint 22 of the tube 12 is positioned to be selectively inserted the second conduit 28 to removably couple the tube 12 to the pipe 16. Other means of coupling the tube 12 to the bag 14 and the pipe 16 are anticipated, such as, but not limited to, quick connects, threaded connections, and the like.

Figure 6:
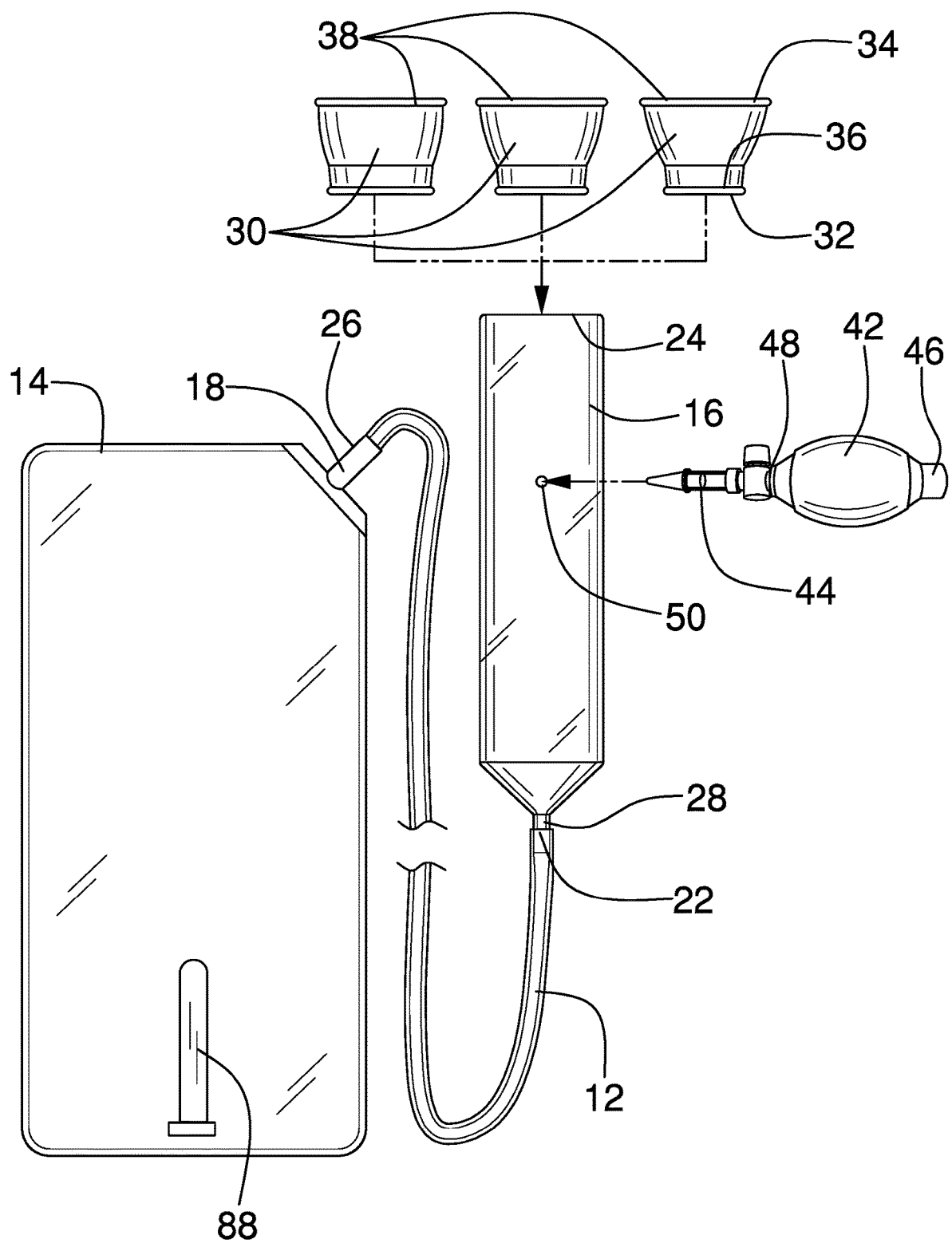
FIG. 6 is a front view of an embodiment of the disclosure.

The device 10 also comprises a set of flanges 30 and a pump 40, as shown in FIG. 6. The flanges 30 comprise at least one of rubber, silicone, and elastomer so that the flanges 30 are resiliently flexible. Each flange 30 is truncated cone shaped so that a first terminus 32 of the flange 30 is circumferentially smaller than a second terminus 34 of the flange 30. Each first terminus 32 of the flanges 30 of the set of flanges 30 has a respective circumference 36 so that the set of flanges 30 comprises flanges 30 with first termini 32 having a variety of circumferences 36, thus positioning a user to select a respective flange 30 that has a first terminus 32 with an associated circumference 36 that is substantially complementary to the penis of the user.

The second terminus 34 is circumferentially complementary to the second end 24 of the pipe 16 so that the pipe 16 is positioned for insertion of the first terminus 32 of the flange 30 into the second end 24 of the pipe 16, positioning the second terminus 34 of the flange 30 proximate to the second end 24 of the pipe 16. The set of flanges 30 may comprise three flange 30, or other number of flanges 30, such as one, two, four, or more flanges 30.

Each of a set of rims 38 is coupled to and extends radially from the second terminus 34 of a respective flange 30 so that the rim 38 is positioned to sealably abut the second end 24 of the pipe 16. The pump 40 is selectively couplable to the pipe 16 so that the pump 40 is in fluidic communication with the pipe 16. The pump 40 is configured to selectively partially evacuate the pipe 16 so that the flange 30 sealably couples to the penis of the user. The sealing of the flange 30 to the penis prevents leakage of urine from the pipe 16.

The pump 40 comprises a bulb 42, a nozzle 44, a selector valve 46, and a release valve 48, as shown in FIG. 6. The selector valve 46 is coupled to the bulb 42. The selector valve 46 is configured to open when the bulb 42 is squeezed in a hand of the user and to close when the hand releases the bulb 42. The release valve 48 is coupled to the bulb 42 and is opposingly positioned relative to the selector valve 46. The nozzle 44 is coupled to the release valve 48 distal from the bulb 42. The nozzle 44 is positioned to be selectively inserted into a hole 50 that is positioned in the pipe 16, thus positioning the user to selectively squeeze the bulb 42 to partially evacuate the pipe 16 so that the flange 30 sealably couples to the penis of the user. The release valve 48 is configured to selectively be opened to admit air into the pipe 16.

The device 10 also comprises a box 52 that defines an interior space 54. The box 52 has a top 56 that is open so that the top 56 is configured to insert the bag 14, the tube 12, the pipe 16, and the pump 40 to stow the bag 14, the tube 12, the pipe 16, and the pump 40 in the box 52.

A lid 58 that is hingedly coupled to the box 52 proximate to the top 56 is positioned to selectively close the top 56 to retain the bag 14, the tube 12, the pipe 16, and the pump 40 in the box 52. A handle 60 that is hingedly coupled to the lid 58 is configured to be grasped in a hand of the user to lift the box 52 and contents thereof.

A pouch 62 is coupled to a lower face 64 of the lid 58 so that an opening 66 of the pouch 62 is positioned to insert a set 68 of the bags 14 to stow the set 68 of the bags 14. Thus, an empty bag 14 is available to the user upon filling of the bag 14 that is coupled to the tube 12. A closure 70 that is coupled to the pouch 62 is positioned to selectively close the opening 66 to retain the set of bags 14 in the pouch 62. The closure 70 may be snap type, as shown in FIG. 3, but also may be of another type, such as, but not limited to, hook and loop type, clasp type, and the like.

Figure 3:
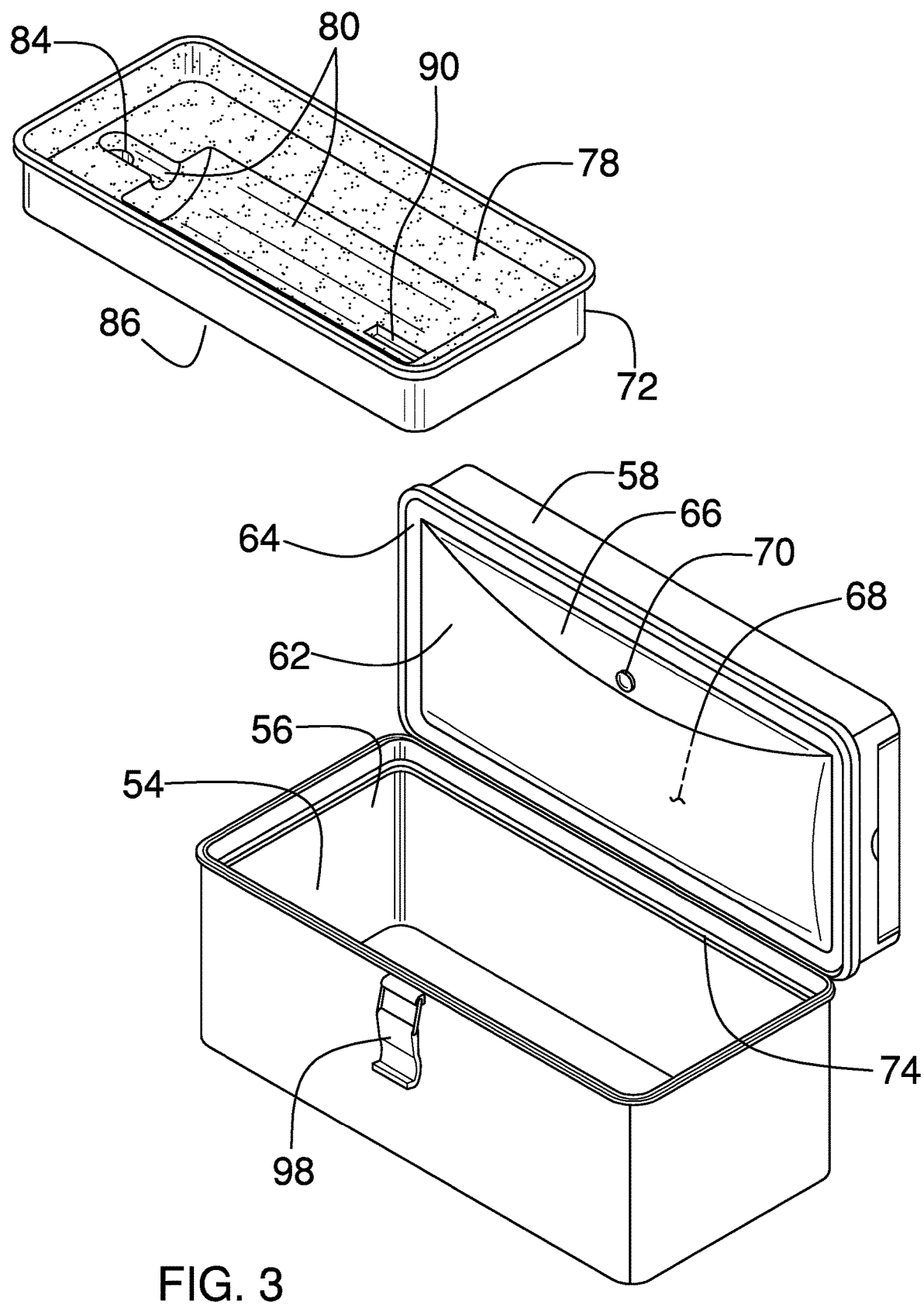
FIG. 3 is an exploded view of an embodiment of the disclosure.
Figure 4:
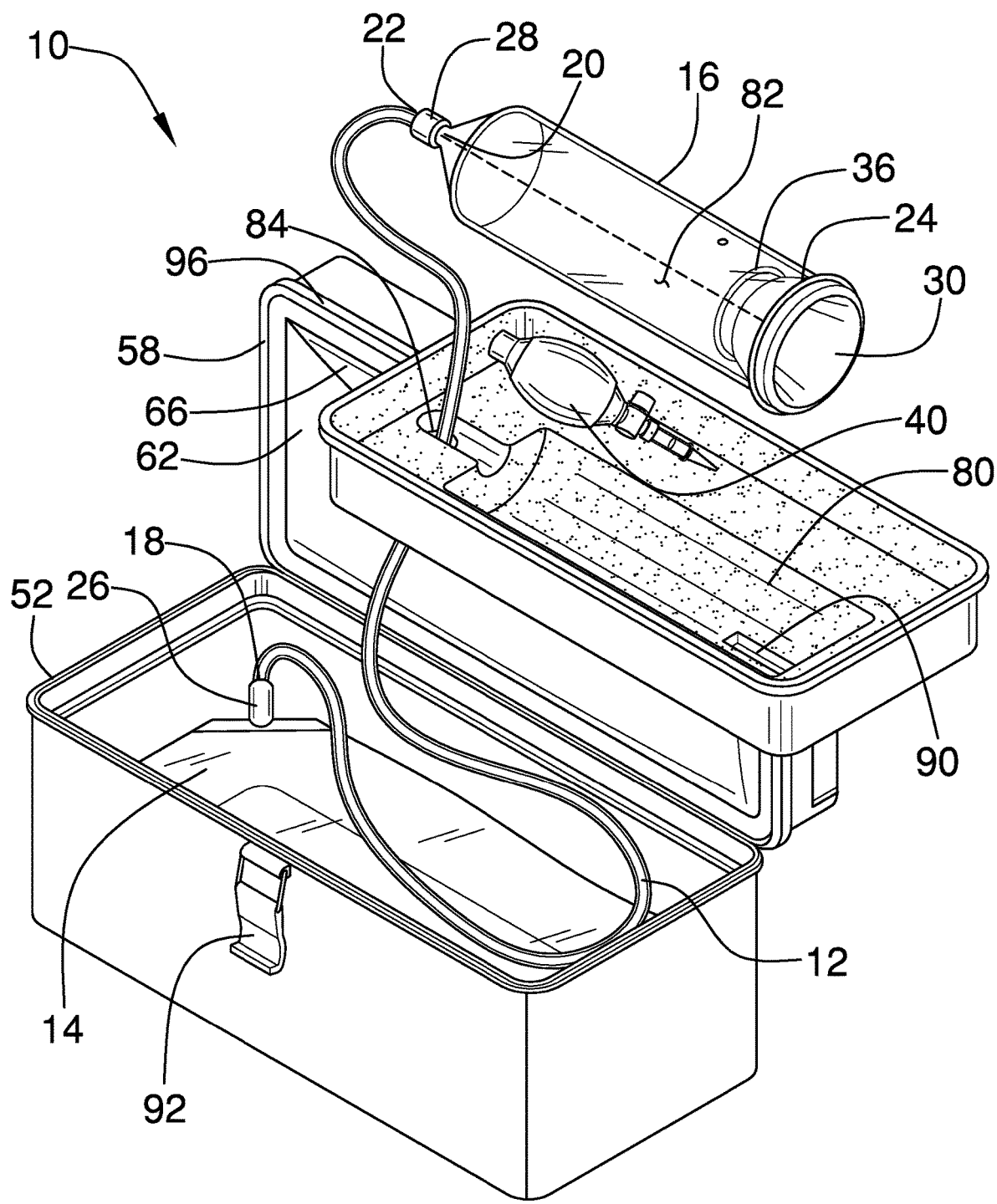
FIG. 4 is a detail view of an embodiment of the disclosure.
Figure 5:
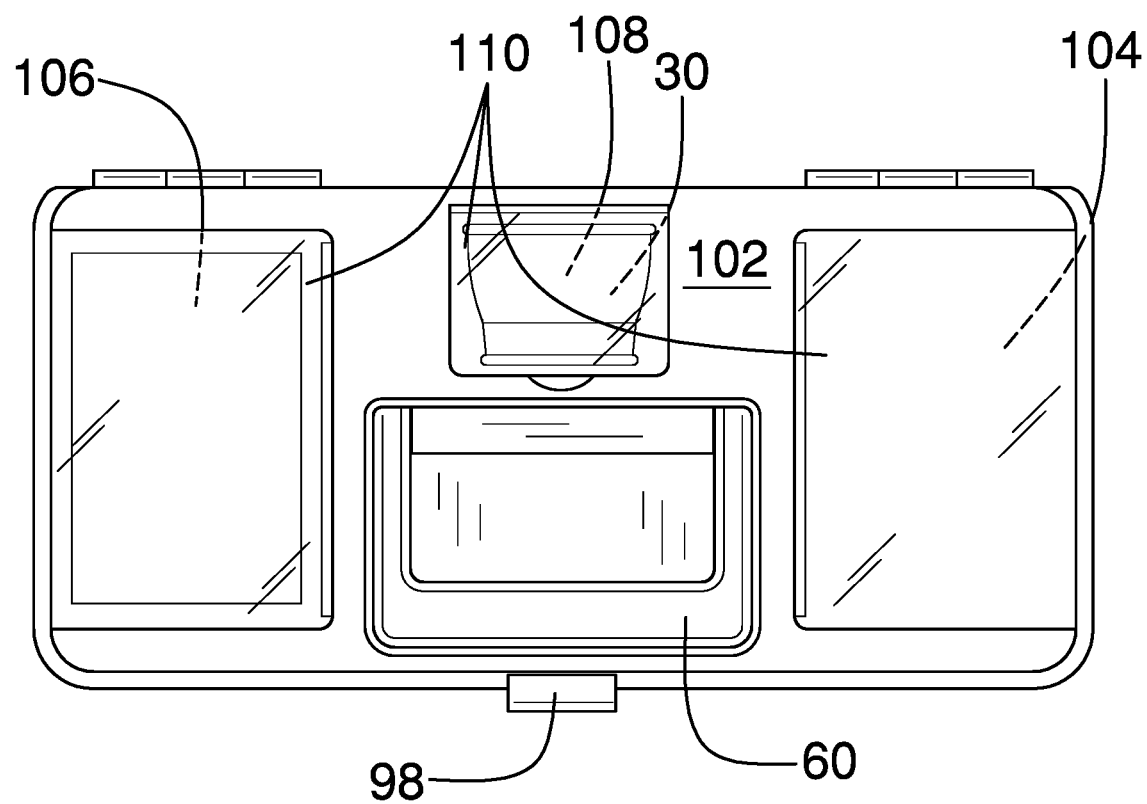
FIG. 5 is a top view of an embodiment of the disclosure.

A tray 72 is selectively insertable into the top 56 of the box 52 so that the tray 72 rests upon a ledge 74 that is positioned in the box 52 proximate to the top 56, as shown in FIG. 3. The tray 72 defines a compartment 76 below the tray 72 that is positioned to stow the bag 14, while the tray 72 is positioned to stow the pipe 16 and the pump 40.

A block 78 that is positioned in the tray 72 comprises at least one of foamed elastomer, rubber, and silicone. A cutout 80 that is positioned in the block 78 is shaped complementarily to a longitudinal cross-section 82 of the pipe 16 so that the cutout 80 is positioned to partially insert the pipe 16 to nest the pipe 16 within the cutout 80.

Figure 7:
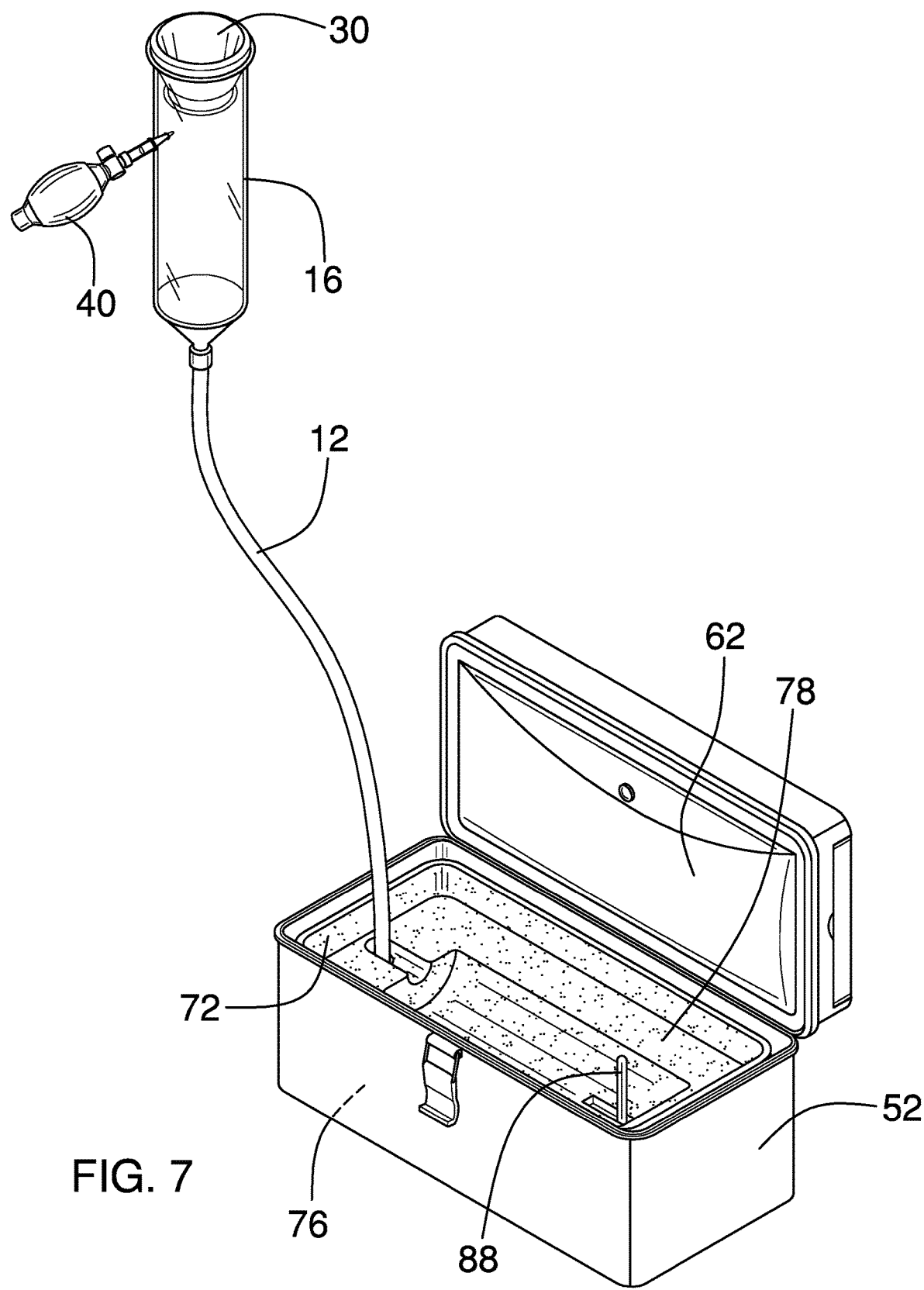
FIG. 7 is an in-use view of an embodiment of the disclosure.
Figure 8:
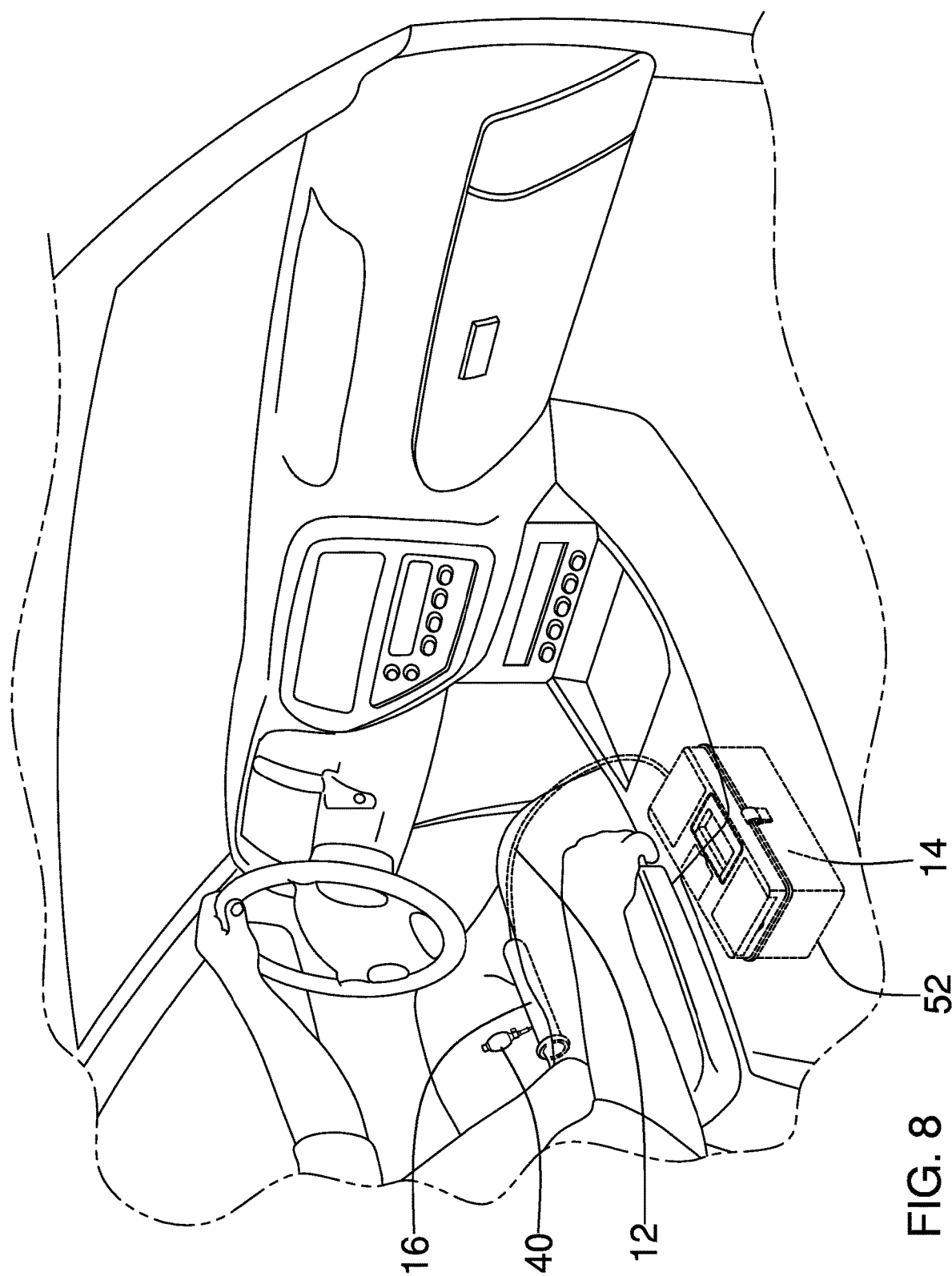
FIG. 8 is an in-use view of an embodiment of the disclosure.

A channel 84 that extends through the block 78 and a lower surface 86 of the tray 72 is positioned for insertion the tube 12 so that the tube 12 is selectively extensible from the compartment 76, as shown in FIG. 7.

An indicator 88, which is spring loaded, is hingedly coupled to the bag 14 and is configured to indicate a level of the urine in the bag 14. A slot 90 that extends through the block 78 and the lower surface 86 of the tray 72 is positioned for selective insertion of the indicator 88, as shown in FIG. 7, so that the indicator 88 is visible to the user with the lid 58 in an open configuration.

Figure 2:
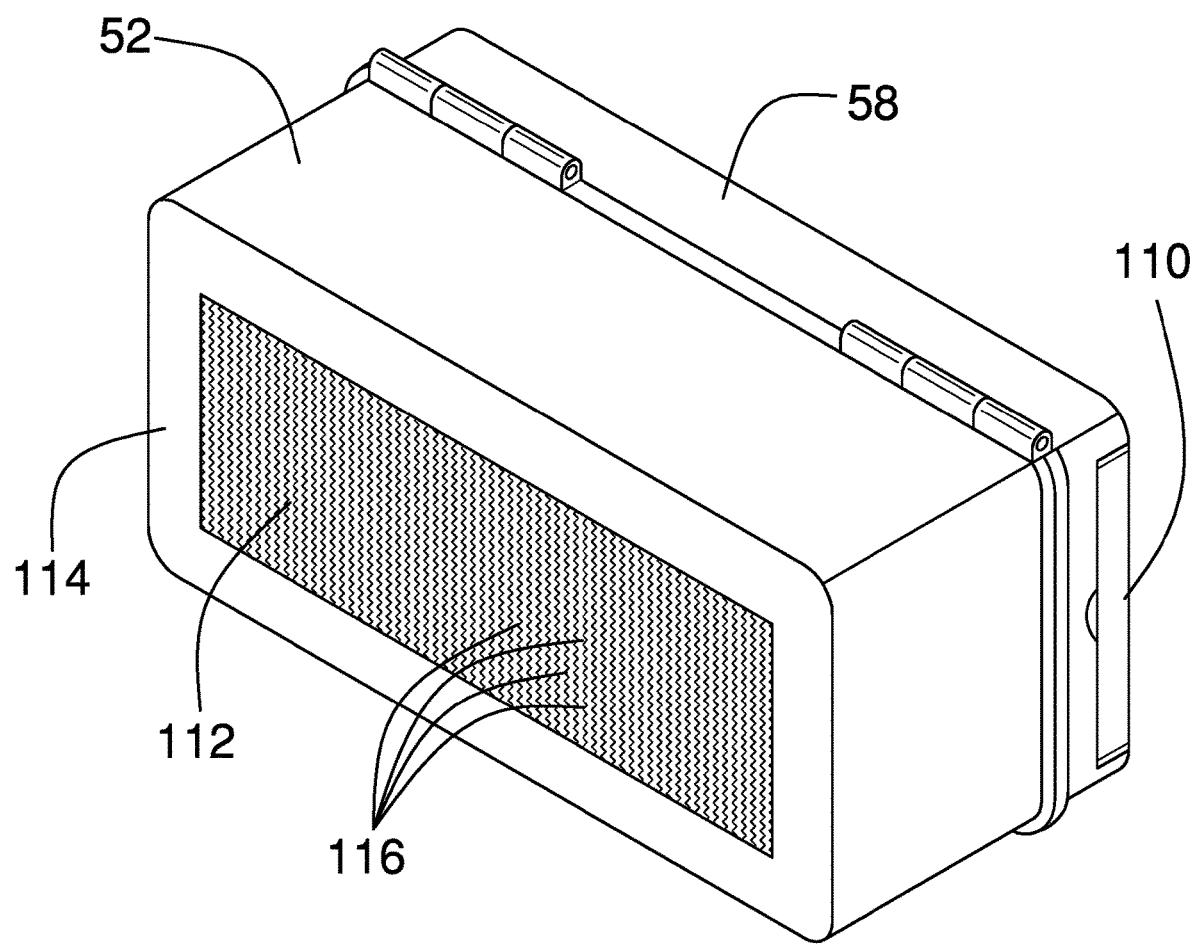
FIG. 2 is an isometric perspective view of an embodiment of the disclosure.

A first connector 92 is coupled to a front edge 94 of the lid 58. A second connector 96 is coupled to the box 52. The second connector 96 is complementary to the first connector 92 so that the second connector 96 is positioned to selectively couple to the first connector 92 to retain the lid 58 in a closed configuration. The second connector 96 and the first connector 92 may comprise a latch closure 98, as shown in FIG. 2, or other closing means, such as, but not limited to, clasp closures, strap closures, and the like.

A set of recesses 100 that extends into an upper face 102 of the lid 58, as shown in FIG. 1, is configured to stow articles. The set of recesses 100 may comprise a first recess 104 that is configured to stow a package of wipes, a second recess 106 that is configured to stow used wipes, and a third recess 108 that is positioned to stow the set of flanges 30. Each of a set of panels 110 is hingedly coupled to the upper face 102 of the lid 58 proximate to a respective recess 100 so that the panel 110 is positioned to selectively close the respective recess.

A fastener 112 that is coupled to a bottom 114 of the box 52 is configured to selectively couple to a surface proximate to the user to removably couple the box 52 to the surface. The device 10 is thus positioned to be easily accessed by the user while driving a vehicle or operating a machine, such as a tractor, airplane, boat, and the like. The fastener 112 may comprise at least one of a plurality of hooks 116, as shown in FIG. 2, and a hook and loop fastener (not shown), or other fastening means, such as, but not limited to, snap connectors, suction cups, and the like. The plurality of hooks 116 is anticipated to be useful in coupling the box 52 directly to carpeting that is positioned proximate to the user, while a hook and loop fastener might have one element coupled to the box 52 and the other element coupled to the surface proximate to the user.

In use, when the user needs to urinate while driving, the lid 58 of the box 52 is opened and the pipe 16 is removed concurrently with the tube 12 being extended from the compartment 76 through the channel 84. The pipe 16 fitted with an appropriately sized flange 30 and then is positioned around the penis of the user. The nozzle 44 of the pump 40 then is inserted into the hole 50 in the pipe 16, positioning the user to partially evacuate the pipe 16 by squeezing the bulb 42. The urine then flows from the pipe 16 through the tube 12 to the bag 14 that is positioned in the compartment 76 below the tray 72.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the elements is present, unless the context clearly requires that there be only one of the elements.

I claim:

1. A urine collection device comprising
a tube, the tube being flexible;
a bag selectively couplable to a first endpoint of the tube;
a pipe selectively couplable by a first end to a second endpoint of the tube such that the pipe is in fluidic communication with the bag wherein a second end of the pipe is configured for inserting a penis of a user for positioning the pipe around the penis enabling the user for urinating into the pipe wherein the tube is configured for flowing of urine from the pipe to the bag;
a set of flanges, the flanges being resiliently flexible, each flange being truncated cone shaped such that a first terminus of the flange is circumferentially smaller than a second terminus of the flange, each first terminus of the flanges of the set of flanges having a respective circumference such that the set of flanges comprises flanges with first termini having a variety of circumferences positioning a user for selecting a respective flange having a first terminus with an associated circumference substantially complementary to the penis of the user, the second terminus being circumferentially complementary to the second end of the pipe such that the pipe is positioned for inserting the first terminus of the flange into the second end of the pipe positioning the second terminus of the flange proximate to the second end of the pipe;
a set of rims, each rim being coupled to and extending radially from the second terminus of a respective flange such that the rim is positioned for sealably abutting the second end of the pipe; and
a pump selectively couplable to the pipe such that the pump is in fluidic communication with the pipe wherein the pump is configured for selectively partially evacuating the pipe such that the flange sealably couples to the penis of the user;
a box defining an interior space, the box having a top, the top being open wherein the top is configured for inserting the bag, the tube, the pipe, and the pump for stowing the bag, the tube, the pipe, and the pump in the box;
a lid hingedly coupled to the box proximate to the top such that the lid is positioned for selectively closing the top for retaining the bag, the tube, the pipe, and the pump in the box;
a handle hingedly coupled to the lid wherein the handle is configured for grasping in a hand of the user for lifting the box and contents thereof;
a ledge positioned in the box proximate to the top;
a tray selectively insertable into the top of the box such that the tray rests upon the ledge defining a compartment below the tray such that the compartment is positioned for stowing the bag and such that the tray is positioned for stowing the pipe and the pump;
a block positioned in the tray, the block comprising at least one of foamed elastomer, rubber, and silicone;
a cutout positioned in the block, the cutout being shaped complementarily to a longitudinal cross-section of the pipe such that the cutout is positioned for partially inserting the pipe for nesting the pipe within the cutout; and
a channel extending through the block and a lower surface of the tray such that the channel is positioned for inserting the tube such that the tube is selectively extensible from the compartment.

2. The device of claim 1, further including the pipe being conically shaped adjacent to the first end such that the urine is directed to the tube.

3. The device of claim 1, further including the pipe being substantially transparent such that urine in the pipe is visible to the user.

4. The device of claim 1, further including the pipe comprising plastic.

5. The device of claim 1, further comprising:
a first conduit coupled to the bag, the first conduit being circumferentially larger than the tube such that the first conduit is positioned for selectively inserting the first endpoint of the tube for removably coupling the tube to the bag; and
a second conduit coupled to the pipe, the second conduit being circumferentially smaller than the tube such that the second endpoint of the tube is positioned for selectively inserting the second conduit for removably coupling the tube to the pipe.

6. The device of claim 1, further including the flanges comprising at least one of rubber, silicone, and elastomer such that the flanges are resiliently flexible, the set of flanges comprising three flanges.

7. The device of claim 1, further including the pump comprising a bulb, a nozzle, a selector valve, and a release valve, the selector valve being coupled to the bulb, the selector valve being configured for opening when the bulb is squeezed in a hand of the user and for closing when the hand releases the bulb, the release valve being coupled to the bulb and opposingly positioned relative to the selector valve, the nozzle being coupled to the release valve distal from the bulb such that the nozzle is positioned for selectively inserting into a hole positioned in the pipe positioning the user for selectively squeezing the bulb for partially evacuating the pipe such that the flange sealably couples to the penis of the user wherein the release valve is configured for selectively opening for admitting air into the pipe.

8. The device of claim 1, further comprising:
a pouch coupled to a lower face of the lid such that an opening of the pouch is positioned for inserting a set of the bags for stowing the set of the bags; and
a closure coupled to the pouch such that the closure is positioned for selectively closing the opening for retaining the set of bags in the pouch.

9. The device of claim 8, further including the closure being snap type.

10. The device of claim 1, further comprising:
an indicator hingedly coupled to the bag, the indicator being spring loaded wherein the indicator is configured for indicating a level of the urine in the bag; and
a slot extending through the block and the lower surface of the tray such that the slot is positioned for selectively inserting the indicator such that the indicator is visible to the user with the lid in an open configuration.

11. The device of claim 1, further comprising:
a first connector coupled to a front edge of the lid; and
a second connector coupled to the box, the second connector being complementary to the first connector such that the second connector is positioned for selectively coupling to the first connector for retaining the lid in a closed configuration.

12. The device of claim 11, further including the second connector and the first connector comprising a latch closure.

13. The device of claim 1, further comprising:
a set of recesses extending into an upper face of the lid wherein the recesses are configured for stowing articles; and
a set of panels, each panel being hingedly coupled to the upper face of the lid proximate to a respective recess such that the panel is positioned for selectively closing the respective recess.

14. The device of claim 13, further including the set of recesses comprising a first recess configured for stowing a package of wipes, a second recess configured for stowing used wipes, and a third recess positioned for stowing the set of flanges.

15. The device of claim 1, further including a fastener coupled to a bottom of the box, the fastener being configured for selectively coupling to a surface proximate to the user for removably coupling the box to the surface.

16. The device of claim 15, further including the fastener comprising at least one of a hook and loop fastener and a plurality of hooks.

17. A urine collection device comprising:
a tube, the tube being flexible;
a bag selectively couplable to a first endpoint of the tube;
a pipe selectively couplable by a first end to a second endpoint of the tube such that the pipe is in fluidic communication with the bag wherein a second end of the pipe is configured for inserting a penis of a user for positioning the pipe around the penis enabling the user for urinating into the pipe wherein the tube is configured for flowing of urine from the pipe to the bag, the pipe being conically shaped adjacent to the first end such that the urine is directed to the tube, the pipe being substantially transparent such that urine in the pipe is visible to the user, the pipe comprising plastic;
a first conduit coupled to the bag, the first conduit being circumferentially larger than the tube such that the first conduit is positioned for selectively inserting the first endpoint of the tube for removably coupling the tube to the bag;
a second conduit coupled to the pipe, the second conduit being circumferentially smaller than the tube such that the second endpoint of the tube is positioned for selectively inserting the second conduit for removably coupling the tube to the pipe;
a set of flanges, the flanges being resiliently flexible, each flange being truncated cone shaped such that a first terminus of the flange is circumferentially smaller than a second terminus of the flange, each first terminus of the flanges of the set of flanges having a respective circumference such that the set of flanges comprises flanges with first termini having a variety of circumferences positioning a user for selecting a respective flange having a first terminus with an associated circumference substantially complementary to the penis of the user, the second terminus being circumferentially complementary to the second end of the pipe such that the pipe is positioned for inserting the first terminus of the flange into the second end of the pipe positioning the second terminus of the flange proximate to the second end of the pipe, the flanges comprising at least one of rubber, silicone, and elastomer such that the flanges are resiliently flexible, the set of flanges comprising three flanges;
a set of rims, each rim being coupled to and extending radially from the second terminus of a respective flange such that the rim is positioned for sealably abutting the second end of the pipe;
a pump selectively couplable to the pipe such that the pump is in fluidic communication with the pipe wherein the pump is configured for selectively partially evacuating the pipe such that the flange sealably couples to the penis of the user, the pump comprising a bulb, a nozzle, a selector valve, and a release valve, the selector valve being coupled to the bulb, the selector valve being configured for opening when the bulb is squeezed in a hand of the user and for closing when the hand releases the bulb, the release valve being coupled to the bulb and opposingly positioned relative to the selector valve, the nozzle being coupled to the release valve distal from the bulb such that the nozzle is positioned for selectively inserting into a hole positioned in the pipe positioning the user for selectively squeezing the bulb for partially evacuating the pipe such that the flange sealably couples to the penis of the user wherein the release valve is configured for selectively opening for admitting air into the pipe;
a box defining an interior space, the box having a top, the top being open wherein the top is configured for inserting the bag, the tube, the pipe, and the pump for stowing the bag, the tube, the pipe, and the pump in the box;
a lid hingedly coupled to the box proximate to the top such that the lid is positioned for selectively closing the top for retaining the bag, the tube, the pipe, and the pump in the box;
a handle hingedly coupled to the lid wherein the handle is configured for grasping in a hand of the user for lifting the box and contents thereof;
a pouch coupled to a lower face of the lid such that an opening of the pouch is positioned for inserting a set of the bags for stowing the set of the bags;
a closure coupled to the pouch such that the closure is positioned for selectively closing the opening for retaining the set of bags in the pouch, the closure being snap type;
a ledge positioned in the box proximate to the top;
a tray selectively insertable into the top of the box such that the tray rests upon the ledge defining a compartment below the tray such that the compartment is positioned for stowing the bag and such that the tray is positioned for stowing the pipe and the pump;
a block positioned in the tray, the block comprising at least one of foamed elastomer, rubber, and silicone;
a cutout positioned in the block, the cutout being shaped complementarily to a longitudinal cross-section of the pipe such that the cutout is positioned for partially inserting the pipe for nesting the pipe within the cutout;

a channel extending through the block and a lower surface of the tray such that the channel is positioned for inserting the tube such that the tube is selectively extensible from the compartment;

an indicator hingedly coupled to the bag, the indicator being spring loaded wherein the indicator is configured for indicating a level of the urine in the bag;

a slot extending through the block and the lower surface of the tray such that the slot is positioned fir selectively inserting the indicator such that the indicator is visible to the user with the lid in an open configuration;

a first connector coupled to a front edge of the lid;

a second connector coupled to the box, the second connector being complementary to the first connector such that the second connector is positioned for selectively coupling to the first connector for retaining the lid in a closed configuration, the second connector and the first connector comprising a latch closure;

a set of recesses extending into an upper face of the lid wherein the recesses are configured for stowing articles, the set of recesses comprising a first recess configured for stowing a package of wipes, a second recess configured for stowing used wipes, and a third recess positioned for stowing the set of flanges;

a set of panels, each panel being hingedly coupled to the upper face of the lid proximate to a respective recess such that the panel is positioned for selectively closing the respective recess; and a fastener coupled to a bottom of the box, the fastener being configured for selectively coupling to a surface proximate to the user for removably coupling the box to the surface, the fastener comprising at least one of a hook and loop fastener and a plurality of hooks.

* * * * *